US00PP31794P2

(12) United States Plant Patent
Esselen et al.

(10) Patent No.: US PP31,794 P2
(45) Date of Patent: May 26, 2020

(54) ORANGE TREE NAMED 'RUBY SL'

(50) Latin Name: *Citrus sinensis*
Varietal Denomination: Ruby SL

(71) Applicant: Crocodile Valley Citrus Co. (Pty) Ltd., Nelspruit (ZA)

(72) Inventors: Leon Leipoldt Esselen, Nelspruit (ZA); Frederik Johannes Veldman, Nelspruit (ZA); Bryan Victor Offer, Nelspruit (ZA)

(73) Assignee: Crocodile Valley Citrus Co. (PTY) Ltd., Nelspruit (ZA)

( * ) Notice: Subject to any disclaimer, the term of this patent is extended or adjusted under 35 U.S.C. 154(b) by 0 days.

(21) Appl. No.: 16/602,179

(22) Filed: Aug. 21, 2019

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./202
CPC ..... A01H 5/08; A01H 6/78
See application file for complete search history.

*Primary Examiner* — Annette H Para
(74) *Attorney, Agent, or Firm* — Michelle Bos Legal LLC

(57) ABSTRACT

'Ruby SL' is a new and distinct orange tree notable primarily for its intensely colored seedless fruit.

4 Drawing Sheets

Genus and species: *Citrus sinensis.*
Variety denomination: 'Ruby SL'.

BACKGROUND AND SUMMARY OF THE VARIETY

The new orange tree 'Ruby SL' resulted from an irradiation-induced limb mutation of 'Ruby Valencia' orange (not patented). Budwood from the irradiated limb was budded onto rootstock to produce second-generation trees, which were planted in 2013. 'Ruby SL' orange tree has been observed and found to retain its distinguishing characteristics through successive asexually propagated generations. Development, selection and asexual propagation of 'Ruby SL' were carried out at Nelspruit, Mpumalanga, South Africa.

'Ruby SL' is a new and distinct orange tree notable primarily for its intensely colored seedless fruit. The fruit size is notably larger than that of its parent 'Ruby Valencia'. Other noticeable differences from the 'Ruby Valencia' include: The 'Ruby SL' tree is not as precocious and produces a smaller yield as compared to 'Ruby Valencia'. 'Ruby SL' is expected to mature earlier than the 'Ruby Valencia' based on trial observations. A comparison of 'Ruby SL' to related and similar varieties is set forth in Table 1.

TABLE 1

Comparison of 'Ruby SL' to Related and Similar Varieties

| Trait | Comparison Variety | Expression of Comparison Variety | Expression of 'Ruby SL' |
|---|---|---|---|
| Tree growth habit | 'Olinda Valencia'* | Spreading | Upright |
| Flesh color | 'Valencia Late'* | Orange | Red |
| Presence of seeds | 'Ruby Valencia' | Seeded | Seedless |
| Fruit size | 'Ruby Valencia' | Smaller | Larger |
| Fruit set | 'Ruby Valencia' | Very precocious | Less precocious |

TABLE 1-continued

Comparison of 'Ruby SL' to Related and Similar Varieties

| Trait | Comparison Variety | Expression of Comparison Variety | Expression of 'Ruby SL' |
|---|---|---|---|
| | | tree, smaller fruit with higher yield | tree, large fruit with lower yield |

*not patented

BRIEF DESCRIPTION OF THE PHOTOGRAPHS

The attached photographs, taken in 2019 at Visalia, Calif., depict 'Ruby SL' fruit and four-year-old 'Ruby SL' trees. Actual colors will vary with lighting conditions; color characteristics of 'Ruby SL' orange should therefore be determined with reference to the observations described herein, rather than from these illustrations alone.

DETAILED BOTANICAL DESCRIPTION

Figure 1:
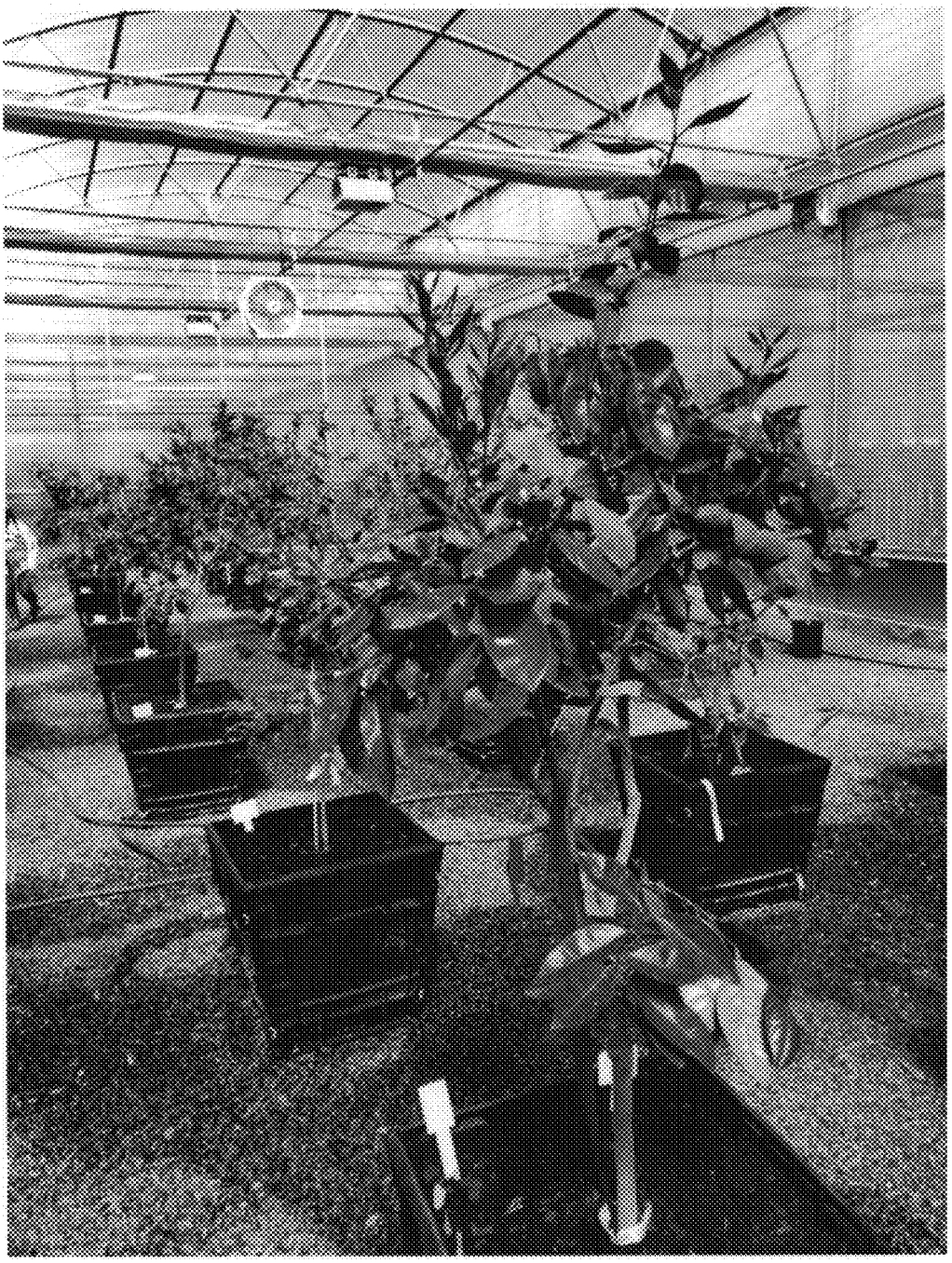
FIG. 1 shows a tree of 'Ruby SL' orange (foreground)
Figure 2:
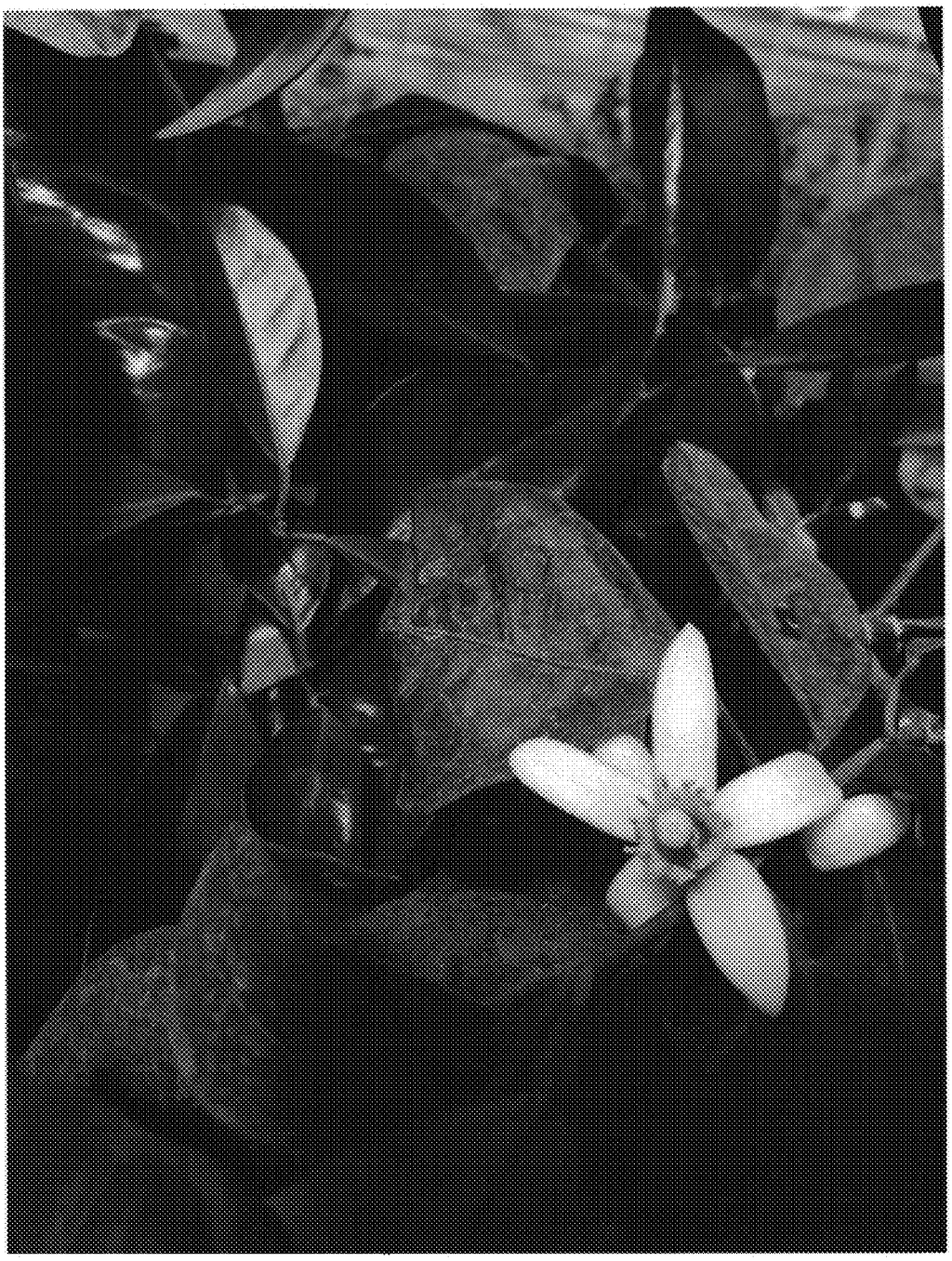
FIG. 2 shows leaves and flower of 'Ruby SL'.
Figure 3:
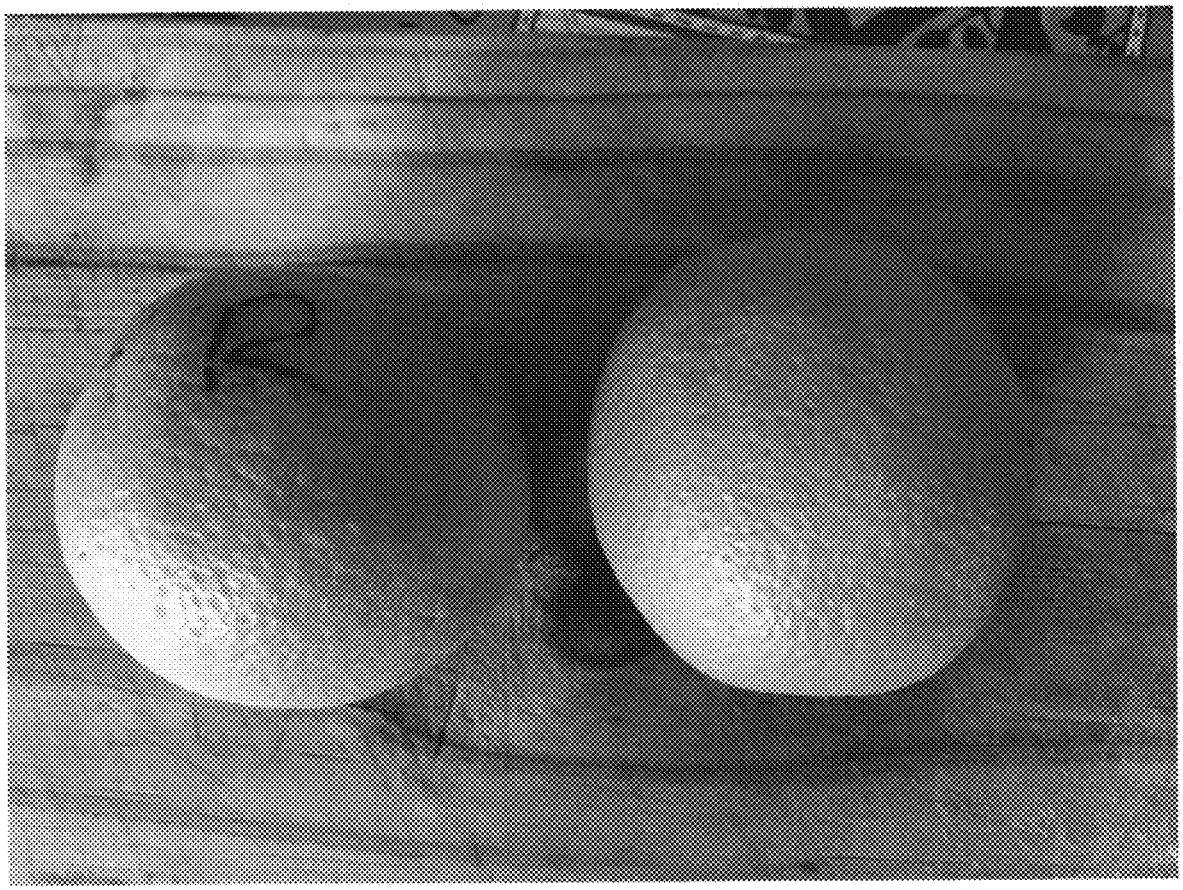
FIG. 3 shows whole 'Ruby SL' orange (bottom) and 'Ruby Valencia' orange (top)
Figure 4:
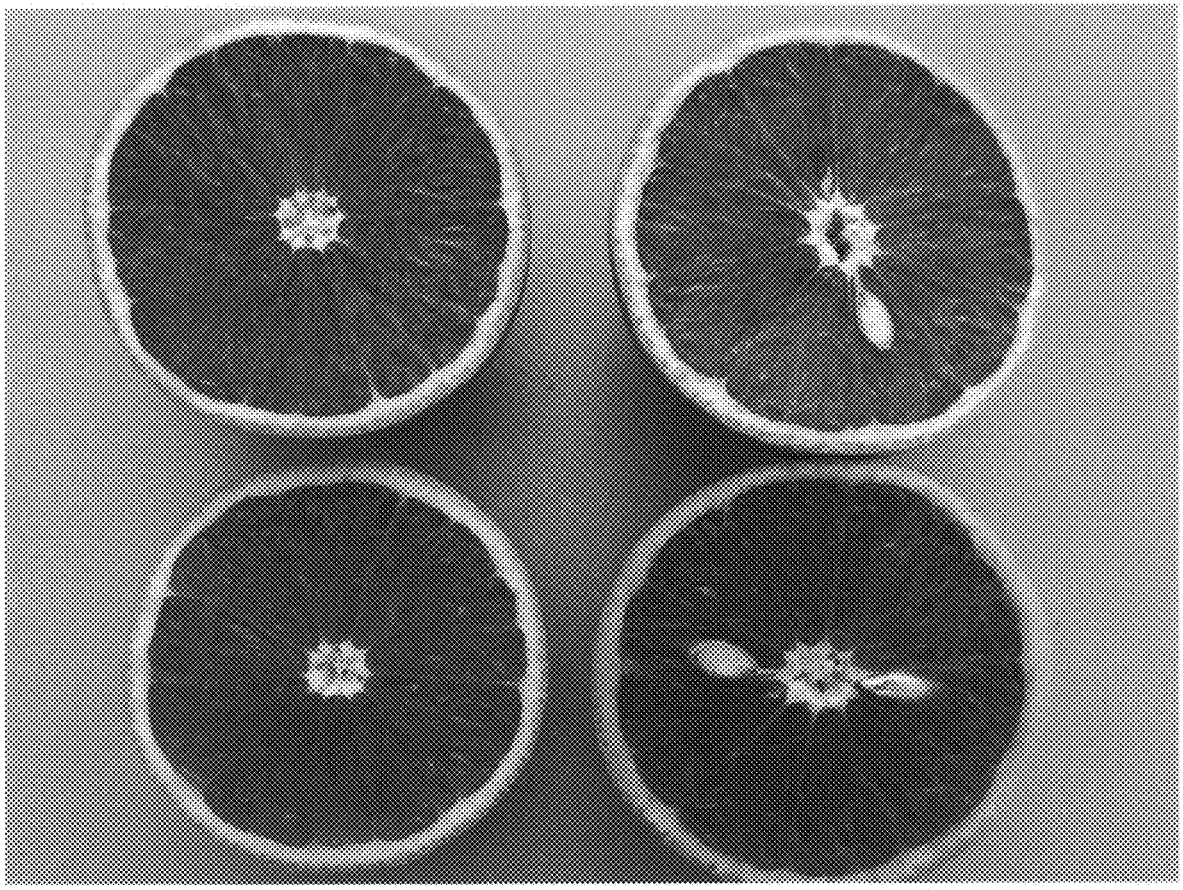
FIG. 4 shows sectioned fruit of 'Ruby SL' orange (right) and 'Ruby Valencia' orange (left).

The following detailed botanical description is based on observations made in 2019 at Visalia, Calif., of four-year-old 'Ruby SL' trees on 'Rough Lemon' rootstock (not patented). The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart (fifth edition).

Tree:

*Vigor*.—Medium.
*Density of canopy*.—Medium.
*Habit*.—Upright.
*Height*.—1.7 m.
*Spread*.—1.1 m.
*Trunk diameter at 30 cm above graft*.—17 mm.
*Bark texture*.—Smooth.
*Bark color*.—Brown 158B.
*Alternate bearing*.—None.
*Chilling requirement*.—None.

Branch (fruiting branches located about 1 m above graft union):

*Length*.—1.0 m.
*Diameter*.—8 mm to 10 mm.
*Crotch angle*.—Narrow to medium.
*Bark color*.—Medium greyed-green 197C.
*Bark texture*.—Smooth.
*Thorns*.—Absent.
*Current year shoot length*.—0.5 m.
*Current year shoot color*.—Medium yellow-green 146B.

Flowers:

*Bud shape*.—Ovate.
*Bud length*.—12 mm to 15 mm.
*Bud diameter*.—5 mm to 6 mm.
*Bud color*.—White NN155D.
*Quantity of blossoms per cluster*.—1.
*Blossom diameter*.—50 mm to 52 mm.
*Blossom depth*.—21 mm to 22 mm.
*Pollen color*.—Yellow 7A.
*Sepal length*.—3 mm to 5 mm.
*Sepal width*.—3 mm to 5 mm.
*Sepal shape*.—Triangular.
*Sepal margin*.—Entire.
*Sepal color*.—Upper surface — Green 149C.
*Sepal color*.—Lower surface — Green 149C.
*Quantity of petals per flower*.—5.
*Relative position of petal margins*.—Not touching.
*Petal shape*.—Oblong.
*Petal apex*.—Obtuse.
*Petal margin*.—Entire.
*Petal length*.—22 mm.
*Petal width*.—7 mm.
*Petal color*.—Upper surface — White NN155D.
*Petal color*.—Lower surface — White NN155D.
*Date of first bloom*.—Mar. 11, 2019.
*Date of full bloom*.—Apr. 1, 2019.
*Date of first fruitlet fall*.—May 15, 2019.
*Pedicel length*.—9 mm.
*Pedicel diameter*.—1.5 mm to 2 mm.
*Pedicel color*.—Green 142A.
*Pistil quantity per flower*.—1.
*Pistil length*.—18 mm.
*Pistil color*.—Green 134A, 142C and 149D.
*Anther quantity per flower*.—25.
*Anther length*.—1.
*Anther color*.—Yellow 7A.
*Stigma length*.—2 mm.
*Stigma color*.—Green 149D.
*Style length*.—6 mm to 7 mm.
*Style color*.—Green 142C.
*Ovary length*.—5 mm.
*Ovary diameter*.—4.5 mm.
*Ovary color*.—Green 142A.

Leaves:

*Length*.—129 mm to 169 mm.
*Width*.—57 mm to 87 mm.
*Blade margin*.—Entire.
*Leaf shape*.—Elliptic.
*Apex shape*.—Acute.
*Base shape*.—Cuneate.
*Color of upper surface*.—Green 140A.
*Color of lower surface*.—Green 142A.
*Texture*.—Upper surface — Smooth, glossy.
*Petiole length*.—17 mm to 19 mm.
*Petiole diameter*.—1.5 mm to 2 mm.
*Petiole color*.—Yellow-green 142A.
*Wings*.—Present.
*Wing width*.—7 mm.

Fruit:

*Quantity per cluster*.—1.
*Axial diameter*.—86 mm to 90 mm.
*Apical diameter*.—95 mm to 98 mm.
*Weight*.—175 g to 240 g.
*General shape in profile*.—Spheroid to oblong.
*Navel*.—Absent.
*Rind color*.—Orange 21B.
*Color pattern*.—Solid.
*Oil glands per cm*$^2$.—Approximately 35.
*Oil gland diameter*.—1 mm.
*Rind thickness*.—3 mm to 5 mm.
*Ease of peeling*.—Moderate.
*Rind texture*.—Smooth.
*Albedo thickness*.—2.25 mm to 2.5 mm.
*Quantity of fruit segments*.—10 to 11 per fruit.
*Toughness of segment membrane*.—Medium.
*Juice sac length*.—8 mm to 10 mm.
*Juice sac shape*.—Varies, mostly elongate.
*Juice sac length to width ratio*.—2.5 to 4.0.
*Juice sac color*.—Red 35A.
*Juice soluble solids*.—11 to 13° Brix.
*Relative harvest maturity*.—Late.
*Harvest window*.—May through August.
*Stem length*.—10 mm.
*Stem diameter*.—3 mm.
*Stem color*.—Yellow-green 145B.
*Propensity to split*.—Low.
*Market use*.—Fresh, juice.
*Storageability*.—Good.
*Susceptibility to pests and diseases*.—None noted.

The invention claimed is:

1. A new and distinct variety of orange tree, substantially as illustrated and described herein.

* * * * *